United States Patent [19]

Meert

[11] Patent Number: 5,397,782

[45] Date of Patent: Mar. 14, 1995

[54] METHOD OF TREATING ADDICTION TO ALCOHOL

[75] Inventor: Theo F. Meert, Rumst, Belgium

[73] Assignee: Janssen Pharmaceutica N.V., Beerse, Belgium

[21] Appl. No.: 259,738

[22] Filed: Jun. 10, 1994

Related U.S. Application Data

[63] Continuation of Ser. No. 708,595, May 31, 1991, abandoned, which is a continuation-in-part of Ser. No. 537,175, Jun. 13, 1990, abandoned.

[51] Int. Cl.$^6$ ............................................ A61K 31/505
[52] U.S. Cl. .................................. 514/258; 514/259; 514/811
[58] Field of Search .................... 514/258, 259, 811

[56] References Cited

U.S. PATENT DOCUMENTS 4,847,281  7/1989  Tyers .................................. 514/397

OTHER PUBLICATIONS

Nabeshima, T. et al., Biochem Pharmacol 37(17): 3277-3284, 1988 (Abstract).

B. S. Neal et al.: "The serotonin$_2$ antagonist ritanserin blocks quasi-morphine withdrawal at a time when mianserin is no longer effective", Psychopharmacology, 100, No. 2, Feb. 1990, pp. 258-266.

J. Duysens et al., "Pharmacological suppresion of the hindlimb withdrawal reflex of the rat; a comparison between serotonergic antagonists and an adrenergic agonist", Arch. Int. Pharmacodyn. Ther., 290, No. 1, 1987, pp. 154-155.

S. L. Handley et al., "Ritanserin Reduces Morphine, and Clonidine, Withdrawal Tics", Brit. J. Pharmacol., 89, Proc. suppl., 1986, p. 647P.

Meert et al., "Ritanserin Reduces Abuse of Alcohol, Cocaine, and Fentanyl in Rats", Pharmacopsychology, 24, No. 5, Sep. 1991.

Meert et al., The preference for alcohol and cocaine is virtually abolished by the 5-HT$_2$ receptor antagonist ritanserin, European Journal of Pharmacology, 183, Jul. 1990 (XIth International Congress of Pharmacology, Amsterdam, The Netherlands).

Dugovic et al., Effects of Ritanserin and Chlordiazepoxide on Sleep Alterations in Rats After Withdrawal From Chronic Cocaine Treatment, WFSRS Founding Congress (Abstract form for Sleep Research), Cannes, France, Sep. 21-25, 1991.

Meert et al., Ritanserin reduces alcohol preference and alcohol intake in rats given the choice between 3% alcohol and water, Pharmacol. (Life Sci. Adv.) 1990, 9: 63-69.

The Merck Index, (11th Ed.), Budavari et al. (Editors), "ondansetron", 1989, p. 1082.

P. 30 of SCRIP, No. 1287/8, Apr. 6/8th, 1988.

Meert et al., Psychopharmacology of Ritanserin: Comparison with Chlordiazepoxide, Drug Development Research 18:119-144 (1989).

Nomikos et al., "Effects of *Ritanserin* on the rewarding properties of d-Amphetamine, Morphine and Diazepam Revealed by Conditioned Place Preference in Rats", Pharmacology Biochemistry & Behavior, vol. 30, pp. 853-858 (1988).

*Primary Examiner*—Raymond J. Henley, III
*Assistant Examiner*—M. Moezie
*Attorney, Agent, or Firm*—Charles J. Metz

[57] ABSTRACT

Method of treating addiction to alcohol and symptoms related to withdrawal of said alcohol comprising the administration of certain 4-[bis(halophenyl)methylene]-1-piperidinyl derivatives.

4 Claims, No Drawings

METHOD OF TREATING ADDICTION TO ALCOHOL

CROSS-REFERENCE TO RELATED APPLICATIONS

This application is a continuation of application Ser. No. 07/708,595, filed May 31, 1991, now abandoned, which is a continuation-in-part of application Ser. No. 07/537,175, filed Jun. 13, 1990, now abandoned.

BACKGROUND OF THE INVENTION

It is generally known that the repeated consumption of habit-forming drugs such as alcohol, minor tranquilizers, stimulantia, opiates, hallucinogens, nicotine in many instances leads to different degrees of addiction. Typically, such addiction is characterized by a need or desire to continue the use of the drug and to obtain it, not seldom by all means, and further by a tendency to increase its dosage. This usually results in a psychological and usually a physiological dependence on the effects of such drugs and eventually has a detrimental effect on the addicted individual and on society.

Once a certain degree of addiction is reached, abstention of habit-forming drugs becomes a serious problem and is often accompanied by undesirable physical and/or psychic symptoms. Therefore, an agent decreasing or overcoming such addiction and, if possible, alleviating or removing the symptoms related to the withdrawal of such habit-forming drugs would be highly welcomed, not only by drug addicts, but also by society in general.

SUMMARY OF THE INVENTION

It now has been found that certain 4-[bis(halophenyl)-methylene]-1-piperidinyl derivatives alleviate, supress or overcome addiction to habit-forming drugs and further, once an individual reaches a certain state of addiction, decrease or even remove symptoms related to withdrawal of habit-forming drugs.

DESCRIPTION OF THE INVENTION

The present invention therefore is concerned with a method of treating individuals suffering from addiction to habit-forming drugs, said method comprising administering to said individuals a compound of formula

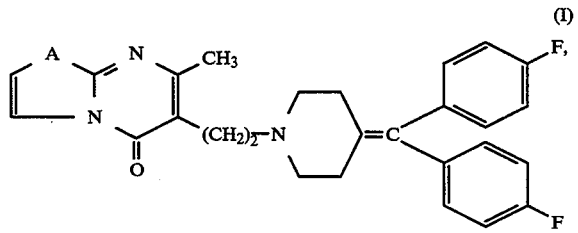

or a pharmaceutically acid addition salt thereof, wherein A represents —CH=CH— or —S—, in an amount effective in alleviating, suppressing or overcoming said addiction. In another aspect, the present invention concerns a method of treating individuals addicted to habit-forming drugs, suffering from symptoms related to the withdrawal or abstention of such drugs, which comprises administering to said persons a compound of formula (I), or an acid-addition salt thereof, in an amount effective in alleviating or overcoming said symptoms.

The compound of formula (I) wherein A is —S—, namely 6-[2-[4-[bis(4-fluorophenyl)methylene]-1-piperidinyl]ethyl]-7-methyl-5H-thiazolo[3,2-a]pyrimidin-5-one is generically designated as ritanserin. The compound of formula (I) wherein A is —CH=CH—, namely 3-[2-[4-[bis(4-fluorophenylmethylene]-1-piperidinyl]ethyl]-2-methyl-4H-pyrido[1,2-a]pyrimidin-4-one is generically designated as seganserin. These compounds as well as their preparation and pharmacological properties are known from U.S. Pat. No. -4,485,107.

The aforementioned term "pharmaceutically acceptable acid addition salt" is meant to comprise those salts obtained by treating the base form of the active ingredients of formula (I) with appropriate acids, such as, for example, inorganic acids, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The term "pharmaceutically acceptable acid addition salt" also comprises the solvates which the compounds of formula (I) may form and said solvates are intended to be included within the scope of the present invention. Examples of such solvates are e.g. the hydrates, alcoholates and the like.

Habit-forming drugs as referred hereinabove comprise various agents such as alcohol; minor tranquilizers such as barbiturates, e.g. pentobarbital, and benzodiazepines, e.g. librium, valium; stimulantia, e.g. cocaine, amphetamines and nicotine; opiates such as fentanyl, alfentanyl and heroine; and hallucinogens, such as LSD; either in pure form or in admixture. Further are comprised products of various kind containing the aforementioned agents such as, for example, the various alcoholic beverages, tobacco, opium, hashish, marijuana and the like. Certain of the aforementioned habit-forming drugs are also referred to as drugs of abuse (or simply as "drugs") or as narcotics.

An individual continuously using these habit-forming drugs usually becomes addicted thereto. In some cases, addiction arises even after having taken the drug only a few times. Individuals being addicted to habit-forming drugs are confronted with a need, desire or longing for such drugs, the strength thereof depending on the individual, the degree of addiction or the kind of drug. In some instances, this need, desire or longing is accompanied by (or causes) a neglecting of the addicted individual's well-being and health, e.g. a loss of apetite, a reduction of mental awareness, social disbehavior and the like. The latter factors too are to be considered as undesired side effects of drug addiction which can be treated by the method according to the present invention.

Individuals thus having become addicted and wanting, or being necessitated, to discontinue the use of habit-forming drugs usually find themselves confronted with a number of undesired symptoms. As symptoms accompanying withdrawal or abstention of habit-forming drugs there may be mentioned a general feeling of discomfort, headache, tremor, anxiety, hallucinations, nausea, vomiting and the like, and in particular a continuous desire or longing for the habit-forming drug having caused the addiction.

The compounds of formula (I) and their acid addition salts are preferably administered formulated in usual pharmaceutical compositions comprising an effective amount of the active ingredient and a suitable pharmaceutically acceptable carrier. Depending on the mode of administration, such compositions may take a variety of forms, e.g. tablets, solutions for parenteral administration, capsules, solutions or suspensions for oral intake, powders and the like. Such compositions are prepared by intimately mixing the active ingredient with one or more suitable carriers and converting this mixture into a form suitable for administration.

The dose to be administered may vary upon the individual which is treated, and is dependent on his or her body size, the degree of addiction and in particular on the kind of habit-forming drug causing the addiction.

A suitable daily dose is contemplated to vary between about 0.1 mg/kg and 50 mg/kg body weight, and in particular between 0.5 and 10 mg/kg body weight, more in particular between 0.5 and 5 mg/kg body weight.

The effectiveness of the compounds of formula (I), as defined above, in overcoming addiction to habit-forming drugs can be demonstrated in the following test procedures.

EXAMPLE 1

Rats forced to drink 3% alcohol for a week followed by a week of alcohol withdrawal, reveal a high preference for alcohol when given the choice between 3% alcohol and water.

The compound ritanserin, given during both the period of alcohol withdrawal and choice between alcohol and water, results in a dose-related reduction in the preference for alcohol. Doses≧0.63 mg/kg body weight ritanserin given subcutaneoulsy once a day, reduced total alcohol consumption as well as the relative preference for alcohol. At 10 mg/kg ritanserin, the highest dose tested, alcohol consumption was reduced with 58% and none of the tested animals had a pronounced preference for alcohol anymore. Simultaneous with the reduction in alcohol consumption, there was an increased water intake, keeping total fluid intake constant. Ritanserin's activity was observed from the first day of choice and the drug remained active during all five test days.

These results indicate that ritanserin can reduce alcohol intake and the alcohol preference without interfering with total fluid intake and without creating an alcohol aversion.

EXAMPLE 2

Rats drinking 0.1 mg/ml cocaine for a week, followed by a week of cocaine withdrawal, reveal a preference for cocaine when given the choice between 0.1 mg/ml cocaine and water in the third week. Ritanserin, given once daily during both the period of cocaine withdrawal and choice between cocaine and water, reduces the preference for cocaine as well as the total amount of cocaine consumed. At 10 mg/kg ritanserin, cocaine intake was reduced by about 30%. Reduction in cocaine intake was accompanied by an increased water consumption keeping total fluid intake constant. Reduction in preference for cocaine remained present at doses down to 2.5 mg/kg ritanserin. However, at the tested doses a complete cocaine aversion was not observed, because the test animals continued to consume some quantity of cocaine. Ritanserin's activity was present from the first day of choice and the drug remained active during the entire period of choice.

EXAMPLE 3

Rats given the choice between fentanyl and water developed a preference for fentanyl after a first period of exposure to fentanyl alone. Ritanserin was administered subcutaneously once daily. At 2.5 mg/kg ritanserin, the highest dose tested, fentanyl intake and fentanyl preference reduced by 50 and 33%, respectively. A reduction of fentanyl preference was observed at doses down to 0.04 mg/kg and was present from the first day of treatment. The reduction in fentanyl intake was compensated by an increase in water drinking. At no time there was a systematic interference of ritanserin with consumatory physiological processes nor did ritanserin create any fentanyl aversion. Furthermore, ritanserin did not affect the discriminative stimulus properties of fentanyl.

I claim:

1. A method of treating individuals suffering from addiction to alcohol to reduce the preference of such individuals for alcohol, said method comprising administering to said individuals a compound of the formula:

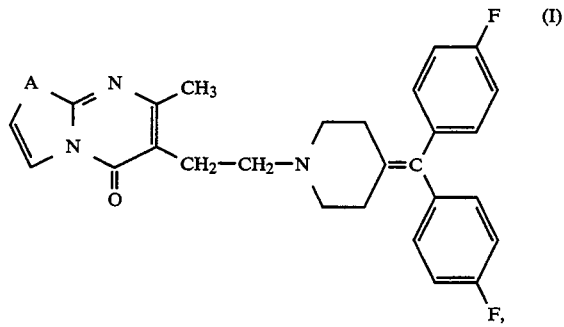

or a pharmaceutically acceptable acid addition salt thereof, wherein A represents —CH=CH— or —S—, in an amount effective to reduce the preference of such individuals for alcohol.

2. A method of treating individuals addicted to alcohol, suffering from symptoms related to the withdrawal or abstention of alcohol, which comprises administering to said persons a compound of formula (I),

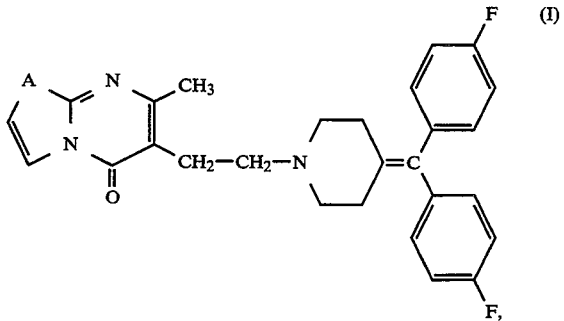

wherein A represents —CH=CH— or —S— or a pharmaceutically acceptable acid addition salt thereof, in an amount effective to reduce the preference of such individuals for alcohol.

3. A method according to claim 1 wherein A is S.
4. A method according to claim 2 wherein A is S.

* * * * *